United States Patent [19]

Lagow

[11] Patent Number: 5,132,455

[45] Date of Patent: Jul. 21, 1992

[54] METHOD FOR SYNTHESIZING PERFLUORINATED ETHER COMPOUNDS VIA POLYESTERS

[75] Inventor: Richard J. Lagow, Austin, Tex.

[73] Assignee: Exfluor Research Corporation, Austin, Tex.

[21] Appl. No.: 642,188

[22] Filed: Jan. 16, 1991

Related U.S. Application Data

[60] Continuation-in-part of Ser. No. 590,304, Sep. 28, 1990, abandoned, which is a continuation-in-part of Ser. No. 147,173, Jan. 22, 1988, abandoned, which is a division of Ser. No. 364,518, Mar. 31, 1982, abandoned.

[51] Int. Cl.$^5$ .............. C07C 51/09; C07C 55/02; C07C 67/00; C07C 69/63
[52] U.S. Cl. .............. 562/583; 560/180; 568/677; 568/683
[58] Field of Search .............. 560/180; 562/583

[56] References Cited

U.S. PATENT DOCUMENTS

| | | | |
|---|---|---|---|
| 3,250,807 | 5/1966 | Fritz et al. | 562/583 |
| 4,113,772 | 9/1978 | Lagow et al. | 562/583 |
| 4,201,876 | 5/1980 | Griffin | 568/677 |
| 4,238,602 | 12/1980 | Griffin | 528/299 |
| 4,647,413 | 3/1987 | Savu | 560/180 |

OTHER PUBLICATIONS

Gerhardt, G., "The Synthesis of Fluorocarbon Monomers and Polymers by Direct Fluorination", Massachusetts Institute of Technology Doctoral Thesis, Jun. 1978.
Persico et al., "Synthesis of Perfluoropolyethers via Hydrocarbon Polyesters: A New General Method", J. Amer. Chem. Soc., 107:1197-1201 (1985).
Persico, D. F. and R. J. Lagow, J. Polymer Sci. 29:233-242 (1991).
Persico, D. F., "New Directions in Elemental Fluorine Chemistry: Novel Fluorocarbons and Perfluoropolymers for Specialized Applications", Doctoral Thesis, Univ. Of Texas at Austin, Chapter VI, May, 1985.

Primary Examiner—J. E. Evans
Attorney, Agent, or Firm—Hamilton, Brook, Smith & Reynolds

[57] ABSTRACT

This invention relates to perfluoroether compounds, and to a general method for creating such compounds. It has been found that such compounds may be created by a three-step method which may be performed using a wide variety of ester starting materials. The first step of the three-step process comprises partial fluorination of a selected polyester compound. This may be performed by contacting the selected polyester with fluorine gas under predetermined conditions until a desired level of partial fluorination is achieved.

The second step of this three-step process involves indirect fluorination to convert the partially fluorinated polyester into partially fluorinated polyether compounds. This step may be conducted by contacting the partially fluorinated polyester with $SF_4$.

The third step of the three-step synethetic process comprises direct fluorination of the partially fluorinated polyether compound at conditions which essentially complete the perfluorinated polyether compound.

By careful selection of the polyester starting compound, this invention provides a general, widely-applicable method of creating perfluoropolyether compounds with selected repeating units and moieties.

5 Claims, 2 Drawing Sheets

METHOD FOR SYNTHESIZING PERFLUORINATED ETHER COMPOUNDS VIA POLYESTERS

RELATED APPLICATIONS

This application is a continuation-in-part of U.S. patent application Ser. No. 07/590,304 filed Sept. 28, 1990, now abandoned, which is a continuation-in-part of U.S. patent application Ser. No. 07/147,173, filed Jan. 22, 1988, now abandoned, which is a divisional application of U.S. patent application Ser. No. 364,518 filed Mar. 31, 1982, now abandoned. The teachings of which are incorporated by reference herein.

BACKGROUND OF THE INVENTION

In general, esters and ethers are organic molecules that contain oxygen in the following structural configuration:

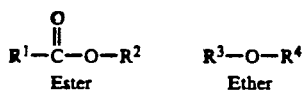

Ester    Ether where $R^1$, $R^2$, $R^3$ and $R^4$ represent organic groups. Esters and ethers may exist in polymeric form, as shown by the following example formulas:

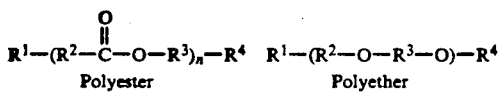

Polyester    Polyether where n represents a large integer, and the material within parentheses represents a "repeating unit" which may contain one or more ester linkages.

It is possible to fluorinate ester to ether compounds. In such a reaction, fluorine atoms are substituted for hydrogen atoms, as exemplified by the following equation:

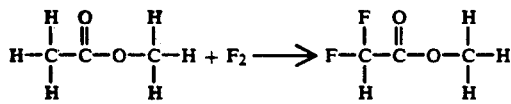

If the fluorine substitution reaction proceeds to completion, i.e., if all of the hydrogen atoms are replaced by fluorine atoms, the resulting compound is designated as "perfluorinated", as exemplified by the following equation:

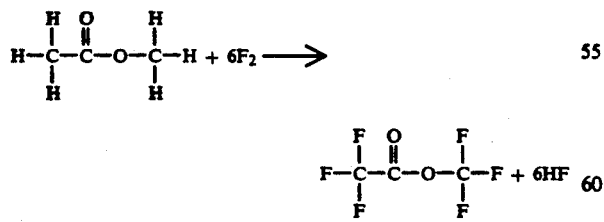

A perfluorinated organic group is referred to herein by the symbol $R_f$, while a partially fluorinated organic group is referred to by the symbol "$R_{h/f}$."

The perfluorination concept also applies to polymers. For example, a "perfluoropolyether" would indicate a polymeric ether molecule wherein all (or substantially all, as described below) of the hydrogen atoms have been replaced by fluorine atoms.

An organic substance may be fluorinated by any of several techniques which are known to those skilled in the art. Such techniques may be divided into two categories, which are commonly referred to as "direct fluorination" and "indirect fluorination".

Direct fluorination implies that a substance is contacted with fluorine that is in the elemental form, as fluorine gas ($F_2$). This type of reaction is highly exothermic, and can lead to adverse effects such as breakage of carbon-carbon bonds. Therefore, direct fluorination is often carried out at low temperatures using fluorine gas which is diluted during the initial contact with inert gas such as helium or nitrogen. See, e.g., U.S. Pat. No. 4,281,119, (Lagow et al., 1981). The concentration of fluorine may be increased gradually or stepwise until pure fluorine gas surrounds the substance. The temperature and pressure of the gas may also be increased during the fluorination process.

Indirect fluorination indicates that the substance to be fluorinated is contacted with a compound that contains fluorine, such as sulfur tetrafluoride ($SF_4$), sulfur hexafluoride ($SF_6$), or molybdenum hexafluoride ($MoF_6$). When heated or otherwise manipulated, such compounds may be induced to release fluorine atoms. The released fluorine atoms react with the contacted substance to produce a desired fluorinated or perfluorinated substance. Several monomeric perfluoroether compounds, and methods for producing such compounds, are known. See, e.g., G. E. Gerhardt et al., *J. Polymer Science: Polymer Chemistry Ed.* 18: 157-168 (1979); U.S. Pat. No. 3,985,810 (von Halasz et al., 1976). Such compounds suffer from the following shortcomings:

1. There are no commonly available perfluorinated polyethers with more than two or three carbon atoms between adjacent oxygen atoms, i.e.,

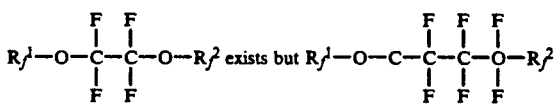

is not commonly available.

2. There are no commonly available perfluorinated polyether compounds with alternating units, e.g.,

3. Most perfluoropolyethers are created by fluorinating perfluoro vinyl epoxide monomers or perfluoroepoxide monomers, e.g.,

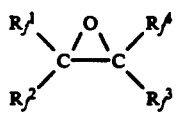

However, it is difficult to synthesize precursor perfluoroepoxides, especially epoxides that contain bulky fluorocarbon groups. It is also difficult or impossible to polymerize perfluoro epoxides containing bulky perfluoro groups ($R_f^1$-$R_f^4$). Either no polymerization occurs or very low molecular weight products are obtained.

Several polymeric perfluoroethers are also know. Such compounds are believed to be highly stable; for example, the only reported reaction of saturated perfluoropolyethers known to the Applicants is chain cleavage at the ether linkage by aluminum chloride at elevated temperatures and high pressure. See, G. V. D. Tiers, *J. Amer. Chem. Soc.* 77: 4837 (1955). Saturated perfluoropolyethers also tend to have relatively broad liquid ranges, with viscosities and surface properties which make them attractive for numerous applications such as solvents, hydraulic fluids, heat-transfer fluids, lubricants, greases, sealants, elastomers and plastics.

It has been shown that various types of polymeric perfluoroethers can be produced by direct fluorination of hydrocarbon polyethers. See, e.g., G. E. Gerhardt, et al., *J. Org. Chem.* 43: 4505 (1978); G. E. Gerhardt, et al., *J.C.S. Perkin I* 1321 (1981). However, the generality of this method is limited by the fact that relatively few hydrocarbon polyether compounds are commercially available. In order to produce a wide range of perfluoropolyether compounds, numerous polymeric precursors with a variety of repeating units would need to be available.

It is possible to create fluoroethers by fluorinating ester compounds. A known reaction for accomplishing this result utilizes $SF_4$ as a fluoridating agent [W. R. Hasek, et al., *J. Amer. Chem. Soc.* 82: 543 (1960); W. C. Smith, *Angew. Chem. Int. Ed.* 1: 467 (1962); W. A. Sheppard, *J. Org. Chem.* 29: 1-11 (1964)] according to the following reaction:

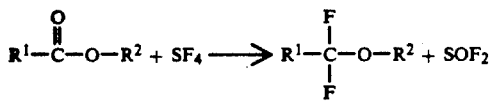

This reaction has been utilized to convert various highly fluorinated monoesters into highly fluorinated monoethers. R. J. De Pasquale, *J. Org. Chem.* 38: 3025 (1973).

The $SF_4$ reaction has also been utilized to create certain forms of polyethers as well. U.S. Pat. No. 4,201,876 (Griffin, 1980); U.S. Pat. No. 4,238,602 (Griffin, 1980). However, the polyether compounds created by $SF_4$ suffered from several limitations:

1. The polyethers were not perfluorinated, and could not be perfluorinated by known techniques without creating substantial quantities of undesired by products.
2. The product of the $SF_4$ reaction has a certain amount reactive acid end groups. The only use that was cited for this compound requires crosslinking and curing steps of convert the compound into an elastomer.

The background art did not provide a general method for creating stable perfluorinated polyethers with a sufficient variety of repeating units.

SUMMARY OF THE INVENTION

This invention is related to polymeric perfluoroether compounds and to a general method for creating such compounds. It has been found that such compounds can be synthesized by a three-step method which can be performed using a wide variety of polyester starting materials. The perfluorinated polyethers produced by the method of this invention are useful as lubricants.

In general, the first step of the three-step process comprises partial fluorination of a selected polyester compound. This can be performed using known techniques, including direct fluorination, which involves contacting the selecting polyester with fluorine gas under predetermined conditions until a desired level of partial fluorination is achieved.

The second step of this three-step process involves indirect fluorination to convert the partially fluorinated polyester into a partially fluorinated polyether. This step can be conducted by contacting the partially fluorinated polyester with $SF_4$. Such contact can be performed at elevated temperatures, or in the presence of other compounds which promote the desired reaction, such as HF gas.

The third step of the three-step synthetic process comprises direct fluorination of the partially fluorinated polyether compound at conditions which essentially complete the perfluorination reaction, thereby creating a perfluorinated polyether compound.

This invention comprises a general method of converting hydrogen-containing polyester compounds into perfluoropolyether compounds. By careful selection of the polyester starting compound, this invention provides a general, widely-applicable method of creating perfluoropolyether compounds with selected repeating units and moieties. Such compounds will have various properties which can be useful for one or more specific applications.

Perfluoropolyethers produced by this method have surface properties and viscosities which make them useful for solvents, hydraulic fluids, heat-transfer fluids, lubricants, greases, sealants, elastomers and plastics. Preferred compounds will have a molecular weight range from about 100 to about 10,000 atomic mass units.

The invention also pertains to the method for synthesizing functional perfluoropolyethers, diacids and diesters. According to the method, a hydrogen-containing polyester is perfluorinated and then reacted with a non-stoichiometric amount of $SF_4$ sufficient to convert the carbonyl groups on the ester to $CF_2$ groups. The resulting perfluoropolyether is then hydrolyzed (to cleave remaining ester groups) or esterified to yield a difunctional perfluoropolyether. The amount of $SF_4$ can be varied depending upon the desired molecular weight of the product and degree of functionalization. It has been shown that increasing amounts of $SF_4$ in the reaction result in higher molecular weight products; however, the degree of functionalization is decreased. Perfluoro diacids of this invention can be used as surfactants.

DETAILED DESCRIPTION OF THE INVENTION

Figure 1:
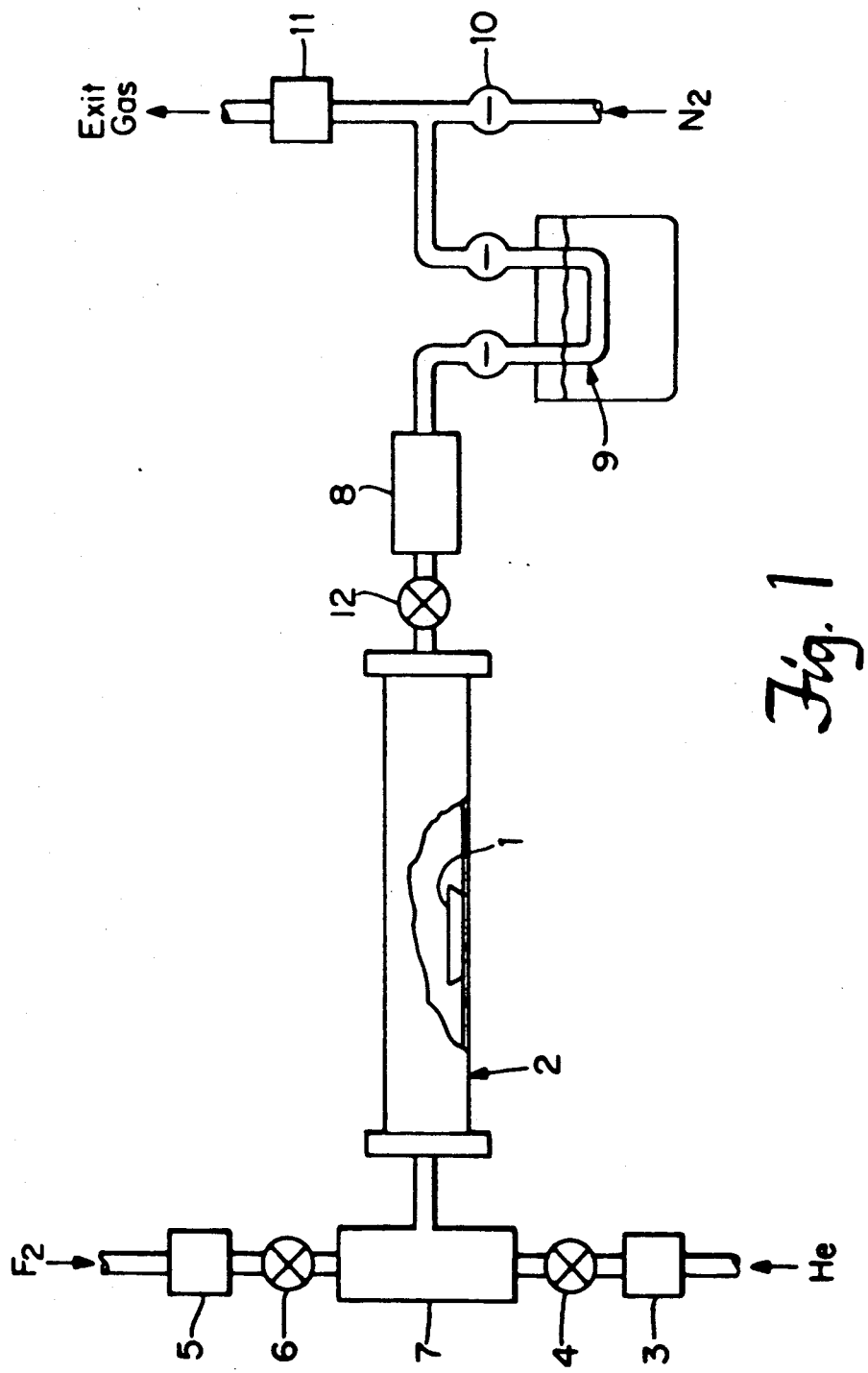
FIG. 1 is a simplified representation of a direct fluorination mechanism.

In one preferred embodiment of this invention, a system which is depicted in FIG. 1 is utilized. A hydrogen-containing polyester compound, such as polybutylene adipate, is utilized as starting material. If the starting material is in solid form, it may be ground or sieved into powdered form if desired. It is loaded into shallow tray 1, often called a "boat". Like all components of the system, the boat should be fabricated of, or coated with, fluorine-resistant material such as nickel or Monel alloy. The loaded boat is placed inside reactor chamber 2, by removing an end plate from the chamber. Reactor chamber 2 is thoroughly flushed with helium gas, which enters the system through flow meter 3 and metering valve 4. If desired, the temperature inside reactor chamber 2 may be reduced or elevated by a variety of means, such as contacting the outside of the chamber with cold or hot liquids. When all oxygen, water and other undesired molecules have been removed from the chamber, fluorine gas enters the system through flow meter 5 and metering valve 6. The fluorine and helium are mixed together in mixing chamber 7 and enter reactor chamber 2. If desired, the system may be equipped with one or more valves, traps or other devices downstream of the reactor chamber. For example, adsorbent trap 8 (as well as the reactor chamber itself) may be filled with particulate sodium fluoride (NaF) to remove hydrogen fluoride (HF) from the gas stream. Condensation trap 9 may be immersed in a cold substance in order to cause volatile substances in the exit gas stream to condense, for analytical, recovery, or other purposes. The system may be protected from oxygen diffusion by adding insert gas (such as nitrogen) through valve 10 under slight pressure. The exit gas may be passed through adsorbent trap 11 to remove unreacted fluorine, and through mineral oil, which turns black when contacted with fluorine, thereby indicating when the adsorbent material in trap 11 should be replaced.

During the initial contact, fluorine gas is diluted with helium. This allows the fluorination reaction to commence slowly, reducing the extent of polyester fragmentation which creates undesired byproducts. The concentration of the fluorine gas is increased in a gradual or stepwise fashion until the desired level of fluorination is achieved. The fluorine flow in continued until the desired degree of fluorination is achieved. If desired, valve 12 may be closed to allow the pressure inside the chamber to be increased. After the fluorine flow is terminated, the system is flushed with helium. The resulting products may then be cured in inert gas at elevated temperature.

The partial fluorination of poly(2,2-dimethyl-1,3-propylene succinate) using this method is represented by the following non-stoichiometric equation:

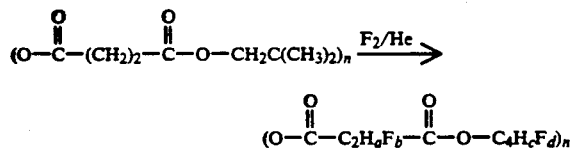

where $a+b+c+d=14$. Although poly(2,2-dimethyl-1,3-propylene succinate) was contacted extensively with pure fluorine gas during experiments by the Applicants, the degree of fluorination (the sum of $b+d$) was usually limited to approximately 12-13 of the 14 hydrogens per repeating unit. Attempts were made to increase the degree of fluorination by increasing the temperature or pressure of the reaction; however, the poly(2,2-dimethyl-1,3-propylene succinate) tended to be converted into undesired byproducts.

The resulting material, designated as hydrofluoropolyester, was cooled and placed in a refrigerated reaction vessel and contacted with anhydrous HF gas. SF$_4$ gas was then transferred by vacuum distillation into the reaction chamber, which was cooled during the process to $-196°$ C. The vessel was then heated to a reaction temperature of about 180° to 190° C., and shaken for a reaction period of about 20 to 24 hours. SF$_4$ reacts with two fluorine atoms, thereby converting ester linkages into ether linkages.

The volatile products were removed by vacuum-line fractionation. The non-volatile oily product was removed from the vessel by adding Freon-113 ™ solvent, and heating and shaking the vessel. The solution thus obtained was filtered and concentrated to approximately one fourth of its volume by distillation. Yellow crystals were filtered out, and subsequently determined to comprise elemental sulfur. The remaining solution was further concentrated by distillation.

The resulting substance, designated as hydrofluoropolyether, was then perfluorinated by direct fluorination, using the system and method described previously utilizing parameters that can be optimized for any specific compounds.

Perfluorination ideally indicates that every hydrogen or other replaceable atom has been replaced by a fluorine atom. However, in actual conditions, it may be difficult or impossible to replace every replaceable atom, or to detect whether every replaceable atom has in fact been replaced. Therefore, perfluorination is used herein in a non-ideal, functional sense to indicate that extensive fluorination has been achieved with the purpose and practical effect of replacing the large majority or substantially all of the hydrogen or other replaceable atoms in a compound with fluorine atoms. For example, an analysis might indicate that the economically optimal material for a given use might be achieved by curtailing the fluorination reaction, thereby reducing expenses, at a given level of fluorination even though it is known that a small percentage of residual hydrogen atoms remain within the compound. Despite the presence of such residual hydrogen atoms, a highly-fluorinated compound of this nature should be regarded as "perfluorinated"; if created by the method of this invention, it would be within the scope of this invention.

As used herein, the terms "ether" and "ester" include molecules with ether linkages (—C—O—C), or ester linkages

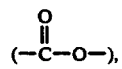

respectively, regardless of whether such molecules also contain other organic or inorganic groups or moieties, such as sulfur linkages or mercaptan groups. As used herein, the terms "diol" and "diacid" include molecules with two or more alcohol groups (R—O—H) or carboxylic acid groups

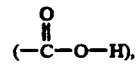

respectively, per molecule, regardless of whether such molecules also contain other organic or inorganic groups or moieties, such as sulfur linkages or mercaptan groups.

This invention provides a practical way of creating perfluoroether compounds that have more than two backbone carbon atoms between other linkages. The only polyether compounds that are currently available utilize monomeric starting materials which are polymerized through vinyl or epoxide reactive sites. Such materials provide polyether compounds with only one or two carbon atoms between oxygen molecules in the backbone chains. In contrast, by selecting polyester starting materials with three or more backbone carbon atoms between ester linkages, it is possible to create perfluoropolyether compounds with three or more backbone carbon atoms between ether linkages using the methods of this invention.

Compounds produced by this method have organic groups between ether linkages which are repeated in a desired sequence, e.g., —($R_A$—O—$R_B$—O—)— where $R_A$ is different from $R_B$. Such compounds may be created by using, as starting material, copolymeric ester compounds (i.e., polyesters formed by polymerizing a mixture of two or more monomeric compounds).

The polyethers can be long, complex, or bulky moieties. Although at least one supplier makes polyether compounds using propyl monomers, such polyethers contain only methyl (—$CH_3$) moieties. By contrast, a wide variety of polyester compounds are available which contain alkyl, aryl, and branched moieties. Such compounds are good candidates for conversion into perfluoropolyethers by the methods of this invention.

The methods of this invention can be used to synthesize functional perfluoropolyether oligomers, diacids, diesters and surfactants from commercially available linear polyesters. Linear polyesters provide a convenient low cost synthesis of such compounds. A reaction scheme starting with hydrocarbon linear polyesters followed by conversion of the ester to a perfluoro ester by direct fluorination and subsequent treatment with nonstoichiometric amounts of sulfur tetrafluoride produce upon hydolysis of ester units remaining in the polymer, low molecular weight perfluoropolyether diacids. Alternatively, this method can be altered to produce diesters and other functional perfluorocarbon intermediates.

The invention will be further illustrated by the following examples:

EXAMPLE 1

Partial Fluorination of Poly(2,2-dimethyl-1,3-propylene succinate)

Poly(2,2-dimethyl-1,3-propylene succinate) (PDPS: Aldrich Chemical Co.), which did not contain fluorine, was sieved to a fine powder, 150 mesh. 2.250 g of powder was placed in a shallow tray made of nickel. The loaded tray was placed in a reactor chamber. The chamber was flushed with helium and then contacted with fluorine as shown in Table 1, under ambient conditions (about 23° C.).

TABLE 1

| Helium Flow cc/min | Fluorine Flow cc/min | Time (days) |
|---|---|---|
| 100 | 0 | 1 |
| 50 | 0.5 | 1 |
| 50 | 1.0 | 1 |
| 20 | 1.5 | 4 |
| 20 | 2.0 | 1 |
| 10 | 3.0 | 1 |
| 5 | 3.0 | 1 |
| 0 | 3.0 | 3 |
| 100 | 0 | 1 |

The weight of the powder increased from 2.520 grams to 5.621 grams. Elemental analysis after products had suffered a slight amount of hydrolysis indicated a carbon content of 25.92% (by weight) and a fluorine content of 58.60%. These indicate that between 12.5 to 13 of the 14 hydrogen atoms per repeating unit had been replaced by fluroine.

Additional ambient temperature experiments were performed using longer contact periods and pressurized pure fluorine. However, the degree of fluorination was not substantially increased over about 13 out of 14 hydrogenatous by such techniques. Elevated temperatures tended to cause the formation of substantial quantities of undesired byproducts.

EXAMPLE 2

$SF_4$ Reaction of Hydrofluoropolyester

Hydrofluoro-PDPS prepared as described in Example 1 was placed in a 75 cc stainless steel sampling cylinder. To avoid hydrolysis, the material was handled in a glove box which had been flushed with inert gas; a container of sodium potassium alloy was placed in the glove box to serve as a dessicating agent. Using a metal, Kel-F vacuum line extension, anhydrous HF and $SF_4$ was vacuum distilled into the cylinder, which had been cooled with liquid nitrogen to $-196°$ C. In a typical reaction 2.0 g of hydrofluoro-PDPS was used (average molecular weight per repeating unit is about 417 which corresponds to about 4.8 millimoles of repeating unit) along with about 20 ml of anhydrous HF and 4.1 g (38 millimoles) of $SF_4$. The loaded cylinder was heated and shaken. The preferred reaction times were about 20 to 24 hours.

If the reaction's volatile products were to be analyzed, they were first transferred by vacuum distillation (all metal system) into a cooled ($-196°$ C.) stainless steel cylinder charged with dry NaF pellets. The cylinder was warmed and shaken for several hours so that all anhydrous HF would be consumed by $NaHF_2$ formation. The remaining volatile species were pumped from the NaF cylinder into the vacuum line and combined with low-volatility, higher molecular weight products from the $SF_4$ reaction cylinder that did not distill into the NaF cylinder but would transfer from the reaction cylinder when subject to a dynamic vacuum for several hours. The combined volatile products were vacuum-line fractionated into $-78°$, $-131°$ and $-196°$ fractions.

The $-196°$ and $-131°$ fractions were shown by infrared analysis to contain mainly unreacted $SF_4$, $SOF_2$ and $SiF_4$. $SOF_2$ is the sulfur containing byproduct of carbonyl to $CF_2$ conversion by $SF_4$, and $SiF_4$ is due to glass etching by inefficient HF removal or HF-producing decomposition of metastable hydrofluoro products. Infrared analysis also indicated the presence of small amounts of fluoroacyl fluorides in the $-131°$ fraction, but separation of these low yield products from the large amount of toxic sulfur-containing species in the fraction would have been difficult, dangerous and of little consequences. The $-78°$ fraction contained (by IR) hydrofluoroacyl fluorides, but gas chromatographic analysis indicated it was a multi-component mixture. From 2 grams of starting hydrofluoropolyester, 350 mg (average of two reactions) of the $-78°$ fraction of inseparable hydrofluoroacyl fluorides were produced. The volatile products of the $SF_4$ reactions were analyzed for only two reactions because separation and analysis of the fluoroorganic species would have been difficult and the nonvolatile oil residue proved to be of greater interest.

The nonvolatile oily product of the $SF_4$ reaction was removed from the reaction cylinder by heating and shaking the cylinder with several 20 ml aliquots of Freon-113 ™ ($CFCl_2CF_2Cl$). The obtained solution was filtered to remove scraps of pipe-thread-sealing teflon tape and some small yellow spheres. The filtered solution was concentrated to approximately ¼ of its volume by distillation, and a small amounts of yellow needle-like crystals was filtered out. The remaining solution was further concentrated by distillation; remaining $CFCl_2CF_2Cl$ solvent was removed by evaporation. A viscous gold-colored oil resulted. For 2.0 g of starting fluoropolyester an average of 1.30 g of this oil was produced.

The yellow spheres and crystals were determined by their melting points of 117°-119° C. and solubilities in benzene and carbon disulfide to be elemental sulfur. Sulfur was obtained in the amount of 50-100 mg from the reactions.

The viscous, nonvolatile oil was analyzed by infrared spectrocopy of a thin oil film cast on a KBr window from $CFCl_2CF_2Cl$ solution. During its workup, no provision for the exclusion of atmospheric moisture was made, so any produced acyl fluoride end-groups or remaining fluorester linkages probably were hydrolyzed to acid end-groups. The infrared spectrum of an $SF_4$ produced oil was compared to the infrared spectrum of a hydrolyzed sample of hydrofluoropolyester. The hydrofluoropolyester was hydrolyzed by dissolving it in tetrahydrofuran and exposing it to atmospheric moisture overnight. Infrared samples were taken of oil films cast from the resulting solution. Based upon comparison of the relative intensities of the carbon-fluorine (1200 cm$^{-1}$) and fluorocarbon acid (1780 cm$^{-1}$) absorptions, the $SF_4$ treated material appeared to be lower in functional group content than the hydrofluoropolyester. The $SF_4$ reaction is therefore believed to have been successful in converting a significant number of ester linkages to ether linkages, i.e., carbonyl to $CF_2$, as expected. In the 3000 cm$^{-1}$ region, broad unassociated acid OH absorption due to remaining hydrogens, were observed. Weak carbonyl absorptions were observed at 1600-1650 cm$^{-1}$ and were presumably due to carboxylate anion end groups.

The non-volatile oil produced by the $SF_4$ reaction were therefore concluded to be a mixture of the functional hydrofluoropolyethers. The lack of volatility and the viscous, oil nature indicated a relatively high molecular weight.

EXAMPLE 3

Perfluorination of Hydrofluoropolyether

In order to obtain the desired perfluoroethers, the material obtained by the process of Example 2 was subjected to additional direct fluorination, using the system and methods described in the specification. Nonvolatile, high molecular weight, non-functional (acyl fluoride) perfluoroethers should result from ambient temperature fluorination. However, conclusive proof of ether formation was desired. Since volatile compounds are more easily separated and identified than nonvolatile compounds, fragmentation fluorination was performed using elevated temperatures as shown in Table 2.

TABLE 2

| He cc/min | $F_2$ cc/min | Temp. (°C.) | Time (hours) |
|---|---|---|---|
| 20 | 2.0 | amb | 24 |
| 5 | 2.0 | 50 | 12 |
| 5 | 4.0 | 50 | 12 |
| 5 | 4.0 | 65-70 | 48 |

The volatile products that resulted were first separated by vacuum line trap-to-trap fractionation into −196°, −131° and −78° fractions. Infrared analysis indicated that the relatively large −196° fraction contained mainly $COF_2$ and $CF_4$, which presumably resulted from decarboxylation and chain end degradation, respectively. The very small −131° fraction contained (by IR) fluoroacyl fluorides.

Higher molecular weight volatile compounds in the −78° fraction were separated by gas/liquid chromatography (GLC). The isolated compounds are listed by their GLC retention time in Table 3 along with their yields and highest m/e peaks in the mass spectra.

The isolated compounds were characterized and identified by infrared, $^{19}F$ NMR and mass spectral analysis. All infrared spectra were very similar to each other and to the infrared spectra of other perfluoroethers. They exhibited the usual strong, broad carbon-fluorine and ether carbon-oxygen absorptions at 1350-1100 cm$^{-1}$ and, also, all showed the same "fingerprint" region absorptions at 1000 cm$^{-1}$ (m), 900 cm$^{-1}$ (m) and 750-700 cm$^{-1}$ (m,broad). The 750-700 cm$^{-1}$ brand resembles the broad band observed at 740-700 cm$^{-1}$ for hydrocarbon alkanes with four sequential methylene (—$CH_2$—) units.

The mass spectra were useful for determining the molecular weights and formulas; the highest mass peak in each spectrum corresponded to the parent minus fluroine fragment. The mass spectra were similar to those of other perfluoroethers in showing extensive fragmentation and rearrangement and in exhibiting the informative high mass peaks only when the spectra were run with the ion source of the spectrometer cooled to ambient temperature. The mass spectra also showed the usual decreasing peak intensity with increasing mass. The common fragment peaks observed were at m/e values corresponding to the following empirical formulas:

$C_nF_{2n+1}$ $C_nF_{2n-1}$ $C_nF_{2n+1}O$ and $C_nF_{2n-1}O$ for all compounds (n = 1 to # of carbon atoms in the compound),
$C_nF_{2n+1}O_2$,
$C_nF_{2n-1}O_2$ for the di- and triethers, and
$C_nF_{2n+1}O_3$ and $C_nF_{2n-1}O_3$ for the triethers The $^{19}F$ NMR signals for the isolated compounds were for the most part broad unresolved multiplets but their chemical shifts and normalized integrated intensities were useful for structure elucidation.

TABLE 3

Compounds Isolated from −78° Fraction of the Volatile Products from the Fluorination of the $SF_4$ Reaction Products

| Compound (GC Retention Time*) | Yield (mg) | Wt. % of −78° Frac. | Highest m/e in Mass Spec. |
|---|---|---|---|
| 22 | 23.3 | 10 | 385 ($C_7F_{15}O$) |
| 75 | 10.5 | 4.5 | 551 ($C_{10}F_{21}O_2$) |
| 77 | 8.2 | 3.5 | 551 ($C_{10}F_{21}O_2$) |
| 86 | 63.7 | 27.2 | 601 ($C_{10}F_{23}O_2$) |
| 97 | 20.2 | 8.6 | 817 ($C_{15}F_{31}O_3$) |
| 100 | 28.3 | 12.1 | 867 ($C_{16}F_{33}O_3$) |

TABLE 3-continued

Compounds Isolated from −78° Fraction of the
Volatile Products from the Fluorination of the SF₄
Reaction Products

| Compound (GC Retention Time*) | Yield (mg) | Wt. % of −78° Frac. | Highest m/e in Mass Spec. |
|---|---|---|---|
| Unseparated Material | 79.8 | 34.1 | — |
| TOTAL | 234 | 100% | |

*GC Program 0° for 20 min., 1°/min. → 100°, 10°/min. → 185°

The $^{19}F$ NMR data is listed in Table 4 with the deduced structures and signal assignments. The key to structure determination was to conclusively establish the identity of one end group by a characteristic $^{19}F$ NMR signal. $CF_3CF_2O$ end groups are indicated by a relatively sharp signal at −133 ppm (due to the internal $CF_2$). $CF_3CF_2O$ end groups are indicated by signals at −90 ppm and −91 ppm (relative intensities 3:2) for the $CF_3$ and $CF_2$ nuclei, respectively. A $CF_3O$ end group has a characteristic signal at approximately −58 ppm. The most common branched end group would be the $(CF_3)_3CCF_2O$ (neopentyl) group. The $CF_3$ nuclei in this group have a chemical shift of −65 ppm while the $CF_2O$ has a shift of −68 ppm giving a relative ratio of 9:2, respectively. The other branched end group $(CF_3)_2CFCF_2O$ has a $CF_3$ chemical shift of −75 ppm while the corresponding $CF_2O$ in this group has a chemical shift of −77 ppm with relative intensities of 6:2, respectively.

Once one end group has been established by using the mass spectral data and knowing that the molecules will be symmetrical with respect to the repeating unit in the higher molecular weight polymer, structure elucidation becomes routine.

The fragmentation fluorination of the $SF_4$ reaction product at this time was of short duration and less severely than possible. This was done so as not to fragment all the oil but leave a nonvolatile, nonfunctional, viscous perfluoro oil in the reactor. An infrared spectrum taken of this oil was similar to that of the volatile products infrared spectrum, as was to be expected. A $^{19}F$ NMR spectrum of this product showed all the chemical shifts indicated in the volatile products $^{19}F$ NMR. The mixture lack of volatility and relatively high viscosity implies that the compounds contained are of a higher molecular weight than the isolated volatile perfluoro ether. Fragmentation conditions may be altered so as to attain a minimum of volatile products and maximize the yield of nonvolatile oil produced by this step. Conditions may also be altered so as to attain a maximum yield of volatile products and a minimum amount of nonvolatile products.

TABLE 4

BRANCHED VOLATILE PERFLUORO ETHERS ISOLATED FROM
FRAGMENTATION REACTION OF POLY(2,2-DIMETHYL-1,3-PROPYLENE SUCCINATE)

| Compound (GC Retention Time) | Assigned $^{19}F$ Chemical Shift in ppm (vs. Ext. CFCl₃) | | Relative Intensities | |
|---|---|---|---|---|
| | | | Obs. | Theor. |
| 1. $(CF_3)_2CFCF_2-O-CF_2CF_2CF_3$  a b c    c e f  (22 min) | a = 73.6  b = n.o.*  c = 76.9 | d = 81.8  e = 130.1  f = 84.6 | a 6  b  c 2  d 2  e 2  f 3.1 | 6  1  2  2  2  3 |
| 2. $CF_3CF_2CF_2-O-CF_2C(CF_3)_2CF_2-O-CF_2CF_3$  a b c    d e f    g h  (75 min.) | a = 83.3  b = 131.3  c = 85.8  d = 67.8 | e = 65.1  f = 67.8  g = 90.3  h = 89.3 | a 3.2  b 2.1  c 2.0  d 2.1  e 5.9  f 2.1  g 1.9  h 3.0 | 3  2  2  2  6  2  2  3 |
| 3. $(CF_3)_3CCF_2-O-CF_2CF_2CF_2CF_2-O-CF_3$  a b    c d e f    g  (77 min) | a = 65.2  b = 68.0  c = 86.0  d = 127.8 | e = 127.8  f = 83.8  g = 57.4 | a 9.1  b 1.9  c 2.1  d 2.0  e 2.0  f 2.1  g 2.9 | 9  2  2  2  2  2  3 |
| 4. $CF_3CF_2CF_2-O-CF_2-C(CF_3)_2CF_2-O-CF_2CF_2CF_3$  a b c    d    e    d    c b a  (86 min) | a = 83.7  b = 131.7  c = 86.1 | d = 68.3  e = 65.5 | a 3.0  b 2.0  c 2.0  d 2.0  e 2.9 | 3  2  2  2  3 |
| 5. $CF_3CF_2CF_2-O-CF_2CF_2CF_2CF_2-O-CF_2C(CF_3)_2CF_2-O-CF_2CF_2CF_3$  a b c    d e e d    f g h    c b a  (97 min) | a = 83.0  b = 131.0  c = 84.5  d = 85.5 | e = 126.7  f = 67.8  g = 65.0  h = 67.8 | a 6.3  b 3.5  c 3.7  d 3.7  e 3.8  f 2.0  g 6.0  h 2.0 | 6  4  4  4  4  2  6  2 |
| 6. $(CF_3)_2CFCF_2-O-CF_2CF_2CF_2CF_2-O-CF_2C(CF_3)_2CF_2-O-CF_2CF_2CF_3$  a b c    d e e d    f g f    h i j  (100 min) | a = 74.9  b = n.o.*  c = 76.8  d = 85.8  e = 126.9 | f = 67.9  g = 65.0  h = 84.6  i = 131.2  j = 83.3 | a 6.1  b  c 2.1  d 3.9  e 4.0  f 4.1  g 5.8  h 2.0  i 1.9 | 6  1  2  4  4  4  6  2  2 |

TABLE 4-continued

BRANCHED VOLATILE PERFLUORO ETHERS ISOLATED FROM
FRAGMENTATION REACTION OF POLY(2,2-DIMETHYL-1,3-PROPYLENE SUCCINATE)

| Compound | Assigned $^{19}F$ | Relative | |
| (GC Retention Time) | Chemical Shift in ppm (vs. Ext. $CFCl_3$) | Intensities | |
| | | Obs. | Theor. |
| | j 2.8 | | 3 |

*not observed

GC Separation with $\frac{1}{8}"\times 25'$ column using fluorosilicone QF-1-0065 on Chromosorb P. Programmed at 0° for 20 min., 1°/min. to 100° C., Helium Flow 100 cc/min.

Based upon the synthetic scheme utilized and the special data obtained on this nonvolatile oil, the main compound of the oil is believed to be perfluoropoly(2,2-dimethyl-1,3-propylene-oxa-tetramethylene oxide) with the following structural formula:

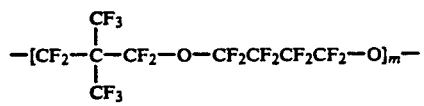

EXAMPLE 4

Perfluoropoly(2,2-dimethyl-1,3-propylene oxide)

2,2-dimethyl-1,3-propanediol was reacted with 2,2-dimethyl malonic acid, in a condensation polymerization to create poly(2,2-dimethyl-1,3-propylene-2,2-dimethylmalonate) according to the following reaction:

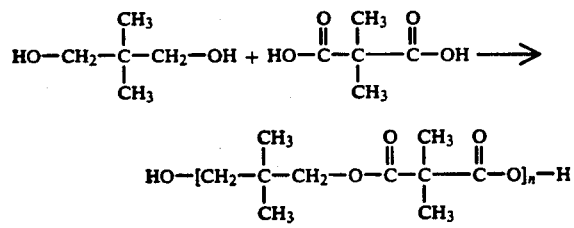

This substance was then contacted with fluorine gas, using the method of Example 1, to create hydrofluoro-poly(2,2-dimethyl-1,3-propylene-2,2-dimethylmalonate). This hydrofluoro-polyester was reacted with $SF_4$, using the method described in Example 2, to create hydrofluoro-poly(2,2-dimethyl-1,3-propylene oxide), a partially fluorinated ether compound. This substance was perfluorinated, using the method of Example 3 to create perfluoropoly(2,2-dimethyl-1,3-propylene oxide) with the following structural formula:

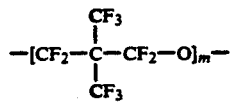

EXAMPLE 5

Perfluoropoly(1,1-dimethylene oxide)

α-hydroxy isobutyric acid was reacted by itself in a condensation polymerization to create poly(isobutyrate) according to the following reaction:

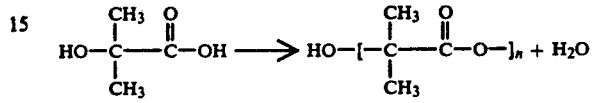

This substance was then contacted with fluorine gas using the method of Example 1, to create hydrofluoro-poly(isobutyrate). This hydrofluoro-polyester was reacted with $SF_4$, using the method described in Example 2, to create hydrofluoro-poly(1,1-dimethylene oxide), a partially fluorinated ether compound. This substance was perfluorinated, using the method described in Example 3, to create perfluoropoly(1,1-dimethylene oxide) with the following structural formula:

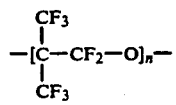

EXAMPLE 6

Perfluoropoly(2,2,4,4-tetramethyl-1,4-butylene oxide)

2,2,4,4-tetramethyl-4-hydroxy butyric acid could be reacted by itself in a condensation polymerization to create poly(2,2,4,4-tetramethyl-butyrate) according to the following reaction:

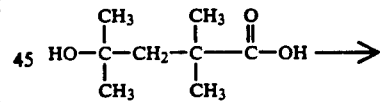

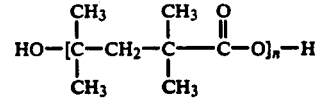

This substance could be then contacted with fluorine gas using the method of Example 1, to create hydrofluoro-poly(2,2,4,4-tetramethyl-butyrate). This hydrofluoro-polyester could be reacted with $SF_4$, using the method described in Example 2, to create hydrofluoro-poly(2,2,4,4-tetramethyl-butylene oxide), a partially fluorinated ether compound. This substance could be perfluorinated, using the method described in Example 3, to create perfluoropoly(2,2,4,4-tetramethyl-1,4-butylene oxide) with the following structural formula:

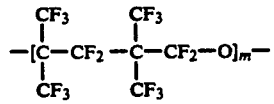

EXAMPLE 7

Perfluoropoly(2,2-di-tertiary-butylethylene oxide)

2,2-di-tertiary-butyl-(α-hydroxy)-acetate acid could be reacted by itself in a condensation polymerization to create poly(2,2-di-tertiary-butylacetate) according to the following reaction:

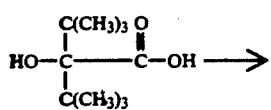

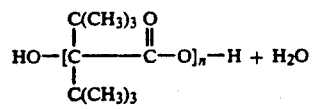

This substance could then be contacted with fluorine gas using the method of Example 1, to create hydrofluoro-poly (2,2-di-tertiary-butylacetate). This hydrofluoro-polyester could be reacted with $SF_4$ using the method of Example 2, to create hydrofluoro-poly(2,2-di-tertiary-butylethylene oxide), a partially fluorinated ether compound. This substance could then be perfluorinated, using the method described in Example 3, to create perfluoro-(2,2-di-tertiary-butylethylene oxide) with the following structural formula:

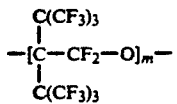

EXAMPLE 8

Perfluoropoly(1,1-dineopentylethylene oxide)

2,2-dineopentyl-(α-hydroxy) acetic acid could be reacted by itself in a condensation polymerization to create poly(2,2-dineopentylacetate) according to the following reaction:

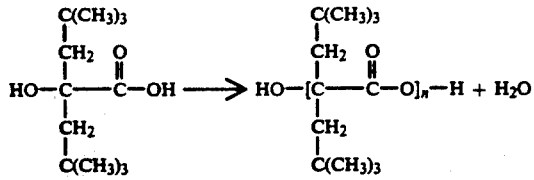

This substance could then be contacted with fluorine gas, using the method of Example 1, to create hydrofluoro-poly(2,2-dineopentylacetate). This hydrofluoropolyester could be reacted with $SF_4$, using the method of Example 2, to create hydrofluoro-poly(1,1-dineopentylethylene oxide), a partially fluorinated ether compound. This substance could then be perfluorinated, using the method described in Example 3, to create perfluoropoly(1,1-dineopentylethylene oxide) with the following structural formula:

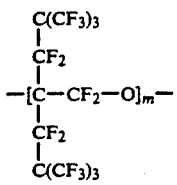

EXAMPLE 9

Perfluoropoly(tetramethylethylene-oxa-2,2-dimethyl-1,3-propylene oxide)

2,2-dimethyl malonic acid could be reacted with 1,1,2,2-tetramethylethylene glycol in a condensation polymerization to create poly(1,1,2,2-tetramethyl-1,2-ethylene-2,2-dimethyl-malonate) according to the following reaction:

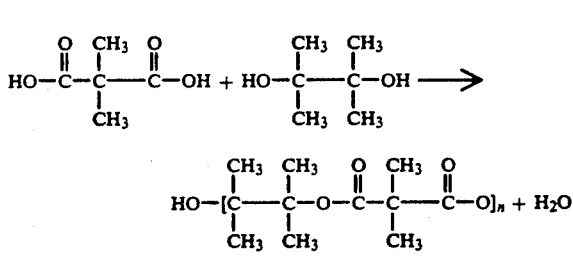

This substance could then be contacted with fluorine gas, using the method of Example 1, to create hydrofluoropoly(1,1,2,2-tetramethyl-1,2-ethylene-2,2,-dimethylmalonate). This hydrofluoro polyester could then be reacted with $SF_4$, using the method described in Example 2, to create hydrofluoro-poly (tetramethylethylene-oxa-2,2-dimethyl-1,3-propylene oxide), a partially fluorinated ether compound. This substance could then be perfluorinated, using the method in Example 3, to create the perfluoropoly (tetramethylethylene-oxa-2,2-dimethyl-1,3-propylene oxide) with the following structural formula:

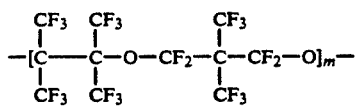

EXAMPLE 10

Perfluoropoly(2,2-propylene-oxa-ethylene oxide)

Acetone could be reacted with oxalic acid in a condensation polymerization to create poly(2,2-propylene oxalate) according to the following reaction:

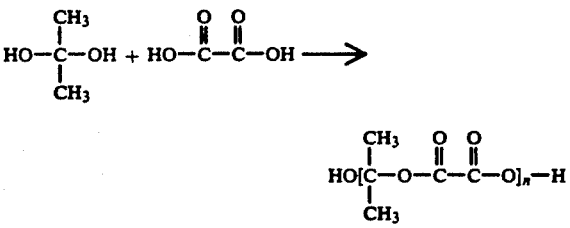

This substance could then be contacted with fluorine gas, using the method of Example 2, to create hydrofluoropoly (2,2-propylene oxalate). This hydrofluoropolyester could then be reacted with SF$_4$, using the method described in Example 2, to create hydrofluoropoly(2,2-propylene-oxaethylene oxide), a partially fluorinated ether compound. This substance could then be perfluorinated, using the method in Example 3, to create perfluoropoly(2,2-propylene-oxaethylene oxide) with the following structural formula:

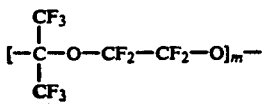

EXAMPLE 11

Synthesis of Functional Perfluoropolyethers

The material prepared in Example 1, or the hydrofluoropolyesters of Example 4 and Example 5, or any other such highly fluorinated polyester can be subjected to the following procedures, as an alternative procedure to those outlined in Example 2.

If, instead of an amount of SF$_4$ in excess of that stoichiometrically necessary to react all carbonyls in the highly fluorinated polyester, such as that used in Example 2 to convert the high molecular weight hydrofluoro- polyester to a high molecular weight hydrofluoro-polyether, stoichiometric or sub-stoichiometric amounts of SF$_4$ are used, ester linkages remain in the highly fluorinated polyether structure. Under these circumstances, care must be taken to replace most of the hydrogen in the initial fluorination step (Example 1) in order to prepare a perfluorinated material.

The resultant perfluoropolymer, after treatment with sub-stoichiometric amounts of SF$_4$, is then hydrolyzed with water. This hydrolysis occurs at the remaining ester linkages and can be acid or base catalyzed. This procedure produces functional diacid perfluoropolyethers, according to the following generalized reaction scheme:

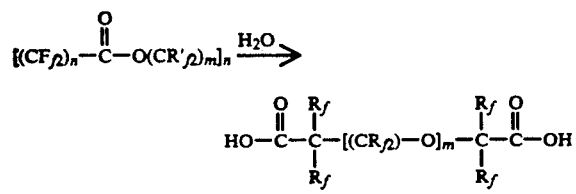

A specific case, for the polyester in Example 1, poly(2,2-dimethyl-1,3-propylene succinate), which would be perfluorinated by separate conditions than those in Table 1, would be as the following scheme indicates:

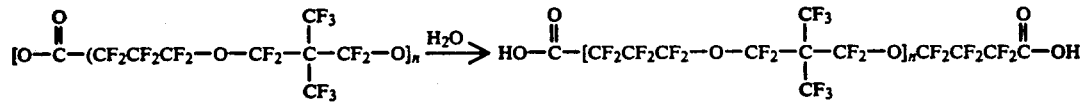

where n is dependent on amount of SF$_4$.

The ratio of moles of SF$_4$ to moles ester functionality in the perfluoroester polymer may be varied. If low molecular weight surfactants are needed, smaller amounts of SF$_4$ are used. If difunctional oligomeric perfluoropolyethers are required then half stoichiometric or stoichiometric amounts of SF$_4$ are used in this procedure.

EXAMPLE 12

Polyethylene succinate was obtained from Eastman Organics and sieved to a powder no less than 150 mesh. The fluorination reaction was carried out as described previously. G. E. Gerhardt and R. J. Lagow, *J. Org. Chem.*, 43, 4504 (1979) and G. E. Gerhardt and R. J. Lagow, *J. Chem. Soc., Chem. Commun.*, 8, 259 (1977).

2.0 grams of polyethylene succinate were fluorinated according to the conditions in Table 5 and 3.2 grams of perfluoropolyester were obtained. The elemental analysis of the reaction product was: C, 25.45%; F, 52.92%; H, 0.11%. The oxygen content of 22.52% was calculated based on the difference (oxygen analysis is difficult in the presence of fluorine).

TABLE 5

POLYETHYLENE SUCCINATE FLUORINATION CONDITIONS

| He (cc/min) | F$_2$ (cc/min) | Temp (°C.) | Time (days) |
|---|---|---|---|
| 50 | 0.5 | ambient | 2 |
| 50 | 1.0 | 40 | 2 |
| 20 | 2.0 | 60 | 1 |
| 10 | 2.0 | 60 | 1 |
| 0 | 2.0 | 60 | 2 |
| 0 | 2.0 | 80 | 1 |

Reaction with SF$_4$ and Subsequent Esterification

The fluorinated polyethylene succinate was handled in a dry box to prevent hydrolysis. A typical SF$_4$ reaction required the use of 0.50 grams of fluorinated polyethylene succinate. The material was placed in a 10 cc stainless steel sample cylinder which was equipped with a Monel valve. Anydrous HF (8 cc) was transferred from a Kel-F container by means of a stainless steel extension of the vacuum line into the cooled ($-196°$ C.) cylinder. The desired amount of SF$_4$ was measured into a Pyrex bulb (2.07 liter) (assuming ideal behaviour) and transferred by vacuum to the cooled sample cylinder. The loaded cylinder was subsequently heated (approx. 180° C.) in a rotating reaction container for 20–24 hours.

After the reaction was completed the volatile constituents (mainly unreacted SF$_4$, HF and SOF$_2$) were vacuum distilled through a trap containing NaF. HF absorbs on NaF to form NaHF$_2$. Volatile materials which were not reacted were caught in a liquid nitrogen trap on the vacuum line and later vented through a caustic solution (1M KOH).

The polyethylene succinate which remained in the sample cylinder was treated with approx. 8 cc of methanol by vacuum distillation of the methanol into the cooled ($-78°$ C.) cylinder. The container was heated (100° C.) and agitated by tumbling during an approx. 12 hours reaction period. The products were filtered through a Celite/Norit bed.

Figure 2:
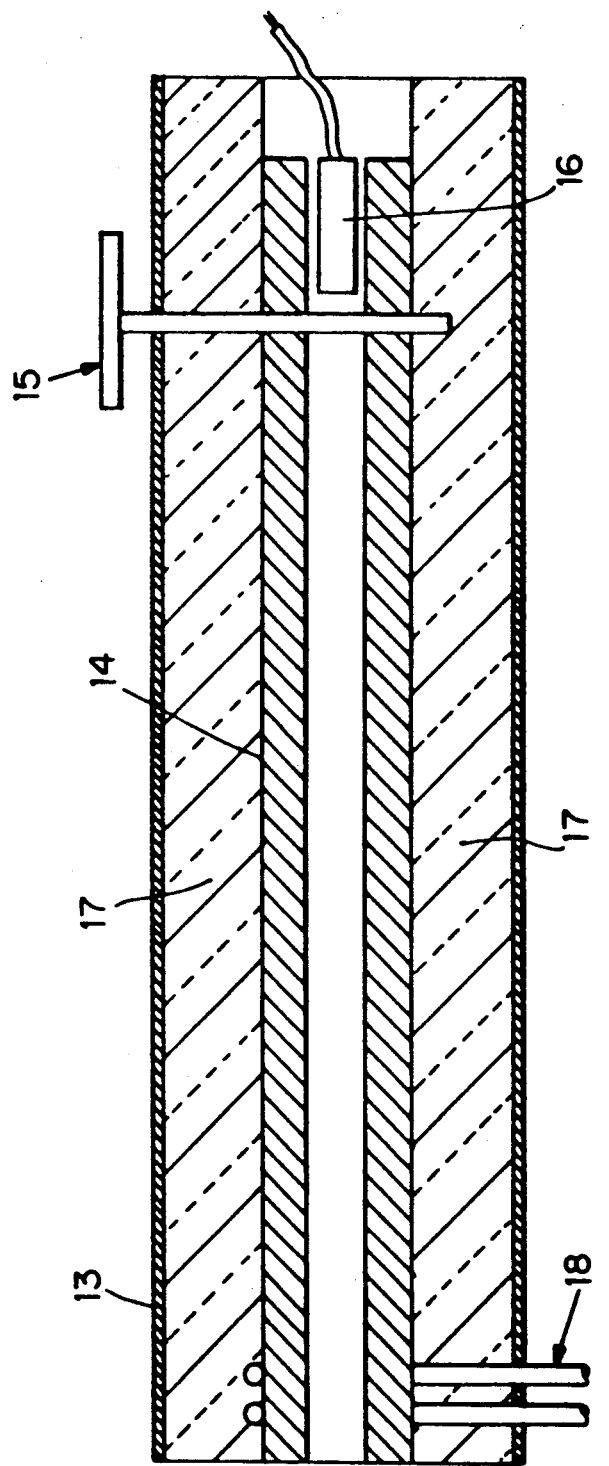
FIG. 2 is a schematic representation of a thermal gradient sublimator.

0% SF$_4$ 0.50 grams of perfluorinated polyethylene succinate were reacted with methanol and subsequently refluxed for 4 hours. The products were determined to be the dimethyl ester of succinic acid and the dimethyl ester of oxalic acid (See Table 6). These two species were separated on a gradient sublimation apparatus (see FIG. 2) in which a continuous temperature gradient is used to obtain selective vapor diffusion of the compounds down a heated tube. The sublimation apparatus comprises an outer steel tube 13 (approx. 3" O.D., 24" length), an inner aluminum tube 14 (approx. 1" O.D.×½") and glass wool 17 therebetween. An appropriate temperature gradient is regulated by cartridge heater 16 (50 Watt/115 V), cooling coils 18 and dial thermometer 15.

The methyl esters of both acids were characterized by parent minus methylated carbonyl ester peaks at m/e 159 and 59 respectively (see Table 6). In the case of the perfluoro succinate ester, a $^{19}$F spectrum was run in methanol using a $CFCl_3$ reference and was found to have a signal at $-120.6$ ppm as expected. Subsequently, in $d^6$-acetone a proton NMR spectra gives a singlet at $\delta 3.97$ for the succininc methyl ester and a peak at $\delta 3.89$ for the oxalic acid ester in agreement with the literature. M. Windholz, ed., The Merck Index, 9th Ed., Merck and Co., Inc. (1976), p. 897. Further comparisons with a mass spectral library for assignment of the compounds gave matching peaks for dimethyl oxalate and dimethyl tetrafluorosuccinate. The yield was 0.22 grams of dimethyl tetrafluorosuccinate.

Alternatively if 0.5 gram of perfluorinated polyethylene succinate was hydrolyzed and placed in the same type of sublimation apparatus at 120° C. for 12 hours, crystalline material was obtained. P-$CO_2H$ peaks were obtained mass spectrometrically at m/e 145 for perfluoro succinic acid and 45 for oxalic acid.

TABLE 6

| SPECTRAL ASSIGNMENTS OF COMPOUNDS FROM 0% SF$_4$ REACTION | | | |
|---|---|---|---|
| Compound | Highest m/e in mass spec | $^{19}$F-NMR (rel. CFCl$_3$) | $^1$H-NMR (rel. TMS) |
| (CF$_2$CO$_2$CH$_3$)$_2$ | 159<br>P—CO$_2$CH$_3$ | $-120.6$ | $\delta 3.91$ |
| (CO$_2$CH$_3$)$_2$ | 59<br>P—CO$_2$CH$_3$ | — | $\delta 3.89$ |
| (CF$_2$CO$_2$H)$_2$ | 145<br>P—CO$_2$H | $-120.3$ | $\delta 11.43$ |
| (CO$_2$H)$_2$ | 45<br>P—CO$_2$H | — | $\delta 9.00$ |

In addition to the mass spectra peak $CF_2CF_2CO_2H^+$, a peak was observed at m/e 100 $C_2F_4^+$ and the base peak at m/e 45 corresponded to $CO_2H^+$. The identity of the perfluoro carboxylic acid was also determined by $CO_2^+$ and fit exactly the spectrum of oxalic acid ($HO_2CCO_2H$) with a computer mass spectrometer assignment. The identity was confirmed by a melting point at 152°-154° C. compared with a value of 157° C. from the literature. M. W. Buxton, D. W. Ingram et al., J. Chem. Soc., 3830 (1952). Further the $^1$H-NMR was run on the oxalic acid dissolved in DMSO $d^6$ and the proton peak at $\delta 9.0$ was close to the peak at $\delta 9.16$ reported in the literature. Sadtler Standard Spectra-Standard NMR Spectra, Sadtler Research Laboratories, Vol. 26, No. 17060 (1973).

25% Stoichiometric SF$_4$

The reaction of 0.50 grams of fluorinated polyethylene succinate and an amount of SF$_4$ corresponding to 25% of the moles ($8.95 \times 10^{-4}$ moles SF$_4$) calculated to react with all carbonyls assuming complete conversion was performed. The products were then esterified with $CH_3OH$ in the manner described above. Infrared analysis of the reaction products was done and the expected strong methyl ester carbonyl absorption at 5.83 microns was observed. The intensity of this carbonyl absorption was diminished in intensity relative to the intensity of the C-F absorption region (7.5-9.7 microns) when compared to that of the 0% SF$_4$ reaction.

The esterified products were separated in the thermal gradient diffusion apparatus (FIG. 2) and the methyl ester of oxalic acid and perfluoro succinic acid were characterized in the same manner as in the first reaction. In addition, a species corresponding to ($MeO_2CCF_2OCF_2CF_2CF_2CO_2Me$) was identified by a decarboxylated parent ion at m/e 275 ($CF_2CF_2CF_2OCF_2CO_2Me^+$) and another positive ion at m/e 209 of the structure ($CF_2CF_2CF_2CO_2Me^+$). Additionally, an ion at m/e 109 corresponding to ($CF_2CO_2Me^+$) and an ion at m/e 59 corresponding to ($CO_2Me^+$) were observed. Also it was clear from observation of very low intensity peaks that higher molecular weight esters were obtained in very low yield. To further characterize the material the $^{19}$F NMR was run in $d^6$-acetone. As indicated in Table 7, the proton NMR gave a value of $\delta 3.96$ clearly showing methyl esterification. When the mixture was studied by $^{19}$F-NMR, before fractional separation in the gradient reactor, end group analysis was under taken comparing the intensity of the signal of the fluorine signal and a number average molecular weight ($M_n$) for the sample was obtained. The $M_n$ was found to be 240.

TABLE 7

| SPECTRAL ASSIGNMENTS OF COMPOUNDS FROM 25% SF$_4$ REACTION | | | |
|---|---|---|---|
| Compound | Highest m/e in mass spec | $^{19}$F NMR | $^1$H NMR |
| (CF$_2$CO$_2$CH$_3$)$_2$ | 159<br>P—CO$_2$CH$_3$ | $-120.6$ | $\delta 3.96^*$ |
| (CO$_2$CH$_3$)$_2$ | 59<br>P—CO$_2$CH$_3$ | — | $\delta 3.96^*$ |
| H$_3$CO$_2$CCF$_2$OCF$_2$CF$_2$CF$_2$CO$_2$CH$_3$<br>a   b  c  d | 275<br>P—CO$_2$CH$_3$ | a 77.8<br>b 83.7<br>c 126.8<br>d 119.1 | $\delta 3.96^*$ |

*Average chemical shift of CH$_3$'s melting point which was observed at 120° C. compared to 118.5° C. in the literature. C. J. Pouchet, ed., Aldrich Library of NMR Spectra, 2nd Ed., Aldrich Chemical Co., Inc., (1983), p. 518.

In addition to the $CO_2H^+$ peak, the oxalic acid spectrum contained a peak at m/e 44 corresponding to

50% Stoichiometric SF$_4$

Infrared analysis showed that after the fluorination reaction and treatment with SF$_4$ on another half gram sample, the relative intensities of the C-F stretch at 7.5-9.7 microns and the carbonyl absorption (5.62 microns) had changed as expected. Separation again was conducted on the thermal gradient device and yielded fractions which gave P-CO$_2$CH$_3^+$ ions at m/e 325 corresponding to the structures [MeO$_2$C(CF$_2$)$_3$O(CF$_2$)$_2^+$] or [MeO$_2$CCF$_2$O(CF$_2$)$_4^+$] and at m/e 491 and m/e 391 corresponding to the decarboxylation of the structure [MeO$_2$C(CF$_2$)$_3$—O(CF$_2$)$_2$O(CF$_2$)$_3$CO$_2$Me] and [MeO$_2$CCF$_2$O(CF$_2$)$_4$OCF$_2$CO$_2$Me]. A further peak at m/e 607 corresponded to the decarboxylation of [MeO$_2$CCF$_2$O(CF$_2$)$_4$OCF$_2$CO$_2$Me]. Fragments of lower m/e values were at 557 (P-CF$_2$CO$_2$Me), 507 (P-(CF$_2$)$_2$CO$_2$Me), and 441 (P-O(CF$_2$)$_3$CO$_2$Me). $^{19}$F— and proton NMR studies were undertaken and chemical shifts are given in Table 8. The proton absorption of the methyl ester is readily apparent at δ3.93. The M$_n$ study by the same $^{19}$F-NMR techniques gave a value for M$_n$ of 527.

which is compatible with the structures proposed in Table 9.

TABLE 9
SPECTRAL ASSIGNMENTS OF COMPOUNDS FROM 100% SF$_4$ REACTION

| Compound | Highest m/e in mass spec | $^{19}$F NMR | $^1$H NMR |
|---|---|---|---|
| (H$_3$CO$_2$CCF$_2$OCF$_2$CF$_2$CF$_2$CF$_2$OCF$_2$)$_2$<br>  a    b  c  c  b    d | 723<br>P—CO$_2$CH$_3$ | a 78.0<br>b 83.3<br>c 125.3<br>d 88.6 | δ3.94* |
| (H$_3$CO$_2$CCF$_2$CF$_2$CF$_2$OCF$_2$CF$_2$OCF$_2$CF$_2$)$_2$<br>  a    b  c    d    d    c  e | 823<br>P—CO$_2$CH$_3$ | a 119.3<br>b 126.6<br>c 83.3<br>d 88.6<br>e 125.3 | δ3.94* |
| H$_3$CO$_2$CCF$_2$O(CF$_2$CF$_2$CF$_2$CF$_2$OCF$_2$CF$_2$O)$_2$CF$_2$CF$_2$CF$_2$CO$_2$CH$_3$<br>  a    b    e c  b    d    d    b  e  f | 939<br>P—CO$_2$CH$_3$ | a 78.0<br>b 83.3<br>c 125.5<br>d 88.6<br>e 126.6<br>f 119.3 | δ3.94* |

*Average chemical shift of CH$_3$'s

300% Stoichiometric SF$_4$

In this sample the ester carbonyl absorptions were of extremely low intensity and occurred at 5.67 microns. The ions of major importance in the mass spectrum were m/e 429 (C$_8$F$_{15}$O$_3$)$^+$, 313 (C$_6$F$_{11}$O$_2$)$^+$, 263 (C$_5$F$_9$O$_2$)$^+$, 219 (C$_4$F$_9$)$^+$, 197 (C$_4$F$_7$O)$^+$, 119 (C$_2$F$_5$)$^+$ base peak and 69 (CF$_3$)$^+$ which are fragments of the oligomeric species [OCF$_2$CF$_2$OCF$_2$CF$_2$CF$_2$CF$_2$O]$_x$. $^{19}$F and $^{13}$C NMR data are given in Table 10. $^{19}$F NMR end group analysis gave a M$_n$ of 2900 for the volatile oil separated by fractional distillation and a heavier oil with a M$_n$ of 3000.

TABLE 10
$^{19}$F AND $^{13}$C CHEMICAL SHIFT ASSIGNMENTS

TABLE 8
SPECTRAL ASSIGNMENTS OF COMPOUNDS FROM 50% SF$_4$ REACTION

| Compound | Highest m/e in mass spec | $^{19}$F NMR | $^1$H NMR |
|---|---|---|---|
| H$_3$CO$_2$CCF$_2$OCF$_2$CF$_2$CF$_2$CO$_2$CH$_3$<br>  a    b  c  d | 275<br>P—CO$_2$CH$_3$ | a 77.8<br>b 84.2<br>c 127.0<br>d 119.0 | δ3.93* |
| H$_3$CO$_2$CCF$_2$CF$_2$CF$_2$O(CF$_2$)$_2$OCF$_2$CF$_2$CF$_2$CO$_2$CH$_3$<br>  a  b  c    d    c  b  a | 491<br>P—CO$_2$CH$_3$ | a 119.0<br>b 127.0<br>c 84.2<br>d 88.7 | δ3.93* |
| H$_3$CO$_2$CCF$_2$OCF$_2$CF$_2$CF$_2$CF$_2$OCF$_2$CO$_2$CH$_3$<br>  a    b  c  c  b    a | 391<br>P—CO$_2$CH$_3$ | a 77.3<br>b 84.2<br>c 125.5 | δ3.93* |
| H$_3$CO$_2$CCF$_2$OCF$_2$CF$_2$CF$_2$CF$_2$OCF$_2$CF$_2$OCF$_2$CF$_2$CF$_2$CO$_2$CH$_3$<br>  a    b  c  c  b    d    d    b  e  f | 607<br>P—CO$_2$CH$_3$ | a 77.3<br>b 84.2<br>c 125.5<br>d 88.7<br>e 127.0<br>f 119.0 | δ3.93* |

*Average chemical shift of CH$_3$'s

100% Stoichiometric SF$_4$

The infrared spectra of the reaction products again show the relative intensity of the carbonyl decreasing with respect to the C-F stretch. In addition to very small amounts of the compounds previously reported in the 50% SF$_4$ reaction, species with decarboxylated parent ions were observed at m/e values 723, 823, and 919. $^{19}$F- and proton NMR studies are reported in Table 9. An $^{19}$F-NMR integration study was used to obtain a M$_n$ and the mixture of products yielded a M$_n$ of 998

FOR THE POLYMER —[(CF$_2$)$_2$O(CF$_2$)$_4$O]—

| Nuclei | $^{19}$F Shift (rel. CFCl$_3$) | | $^{13}$C Shift (rel. TMS) | |
|---|---|---|---|---|
| [OCF$_2$CF$_2$OCF$_2$CF$_2$CF$_2$CF$_2$]$_x$<br> a  a    b  c   c   b | a<br>b<br>c | 88.8<br>83.6<br>125.7 | a<br>b<br>c | 114.9<br>116.4<br>108.9 |
| —OCF$_3$ | | 55.8 | | * |
| —OCF$_2$CF$_2$CF$_3$<br>  a    b   c | a<br>b | 87.7<br>131.0 | | *<br>* |

TABLE 10-continued

| | 19F AND 13C CHEMICAL SHIFT ASSIGNMENTS FOR THE POLYMER —[(CF$_2$)$_2$O(CF$_2$)$_4$O]— | |
|---|---|---|
| Nuclei | $^{19}$F Shift (rel. CFCl$_3$) | $^{13}$C Shift (rel. TMS) |
| c | 82.0 | * |

*$^{13}$C resonance not seen

RESULTS AND DISCUSSION

It has been clearly demonstrated experimentally that as expected with increasing amounts of SF$_4$, the molecular weight of the difunctionalized diester perfluoropolyether increases and the M$_n$ values have increased as one goes from no SF$_4$ to 300% stoichiometric SF$_4$. The values observed were: 0% SF$_4$, 168; 25% SF$_4$, 240; 50% SF$_4$, 527; 100% SF$_4$, 998; 300% SF$_4$, 2900 and 3000. More effective methods are being developed for separation of the functionalized fluorocarbons and surfactants. These include high pressure liquid chromatography, fractional spinning band vacuum distillation and cryogenic (super critical point) separations. Hydrolysis or esterification of the polyether in the absence of SF$_4$ results in the production of dicarboxylic acids. Note that the alcohol rearranges to an acid fluoride which subsequently hydrolyzes because alpha fluoroalcohols and unstable and eliminate HF at temperatures as low as −80° C. In contrast, similar reactions in the presence of high SF$_4$ concentration yield the perfluorinated high molecular weights polyether with little or no functionalization.

EQUIVALENTS

Those skilled in the art will recognize, or be able to ascertain using no more than routine experimentation, numerous equivalents to the specific apparatus and procedures described herein. Such equivalents are considered to be within the scope of this invention, and are covered by the following claims.

It may be possible to assign more than one chemical name to one or more of the substances for which structural formulas are supplied. The claims are intended to cover the ether compounds disclosed by this invention, regardless of the names assigned to such compounds.

I claim:

1. A method for creating a difunctional polyether compound comprising the following steps:
    a) reaction a hydrogen containing polyester with fluorine gas under conditions sufficient to perfluorinate said polyester;
    b) reacting said perfluorinated polyester with sulfur tetrafluoride in an amount sufficient to convert only a portion of the ester linkages on said perfluorinated polyester to ether linkages, thereby producing a perfluorinated polyether compound containing ester linkages; and
    c) hydrolyzing the ester linkages of said functional perfluoropolyether compound to produce a lower molecular weight difunctional perfluoroether compound.

2. A method of claim 1 wherein the ester linkages of said perfluorinated polyether compound are hydrolyzed by reacting said compound with water.

3. A method of claim 2 wherein said hydrolysis is performed in the presence of an acid or a base.

4. A method of claim 2 wherein the product of said hydrolysis is a dicarboxylic acid substituted perfluoropolyether oligomer.

5. A method for creating a difunctional carboxylic acid polyether comprising the following steps:
    a) reacting a hydrogen containing polyester with fluorine gas under conditions sufficient to perfluorinated said polyester;
    b) reacting said perfluorinated polyester with sulfur tetrafluoride in an amount to convert only a small portion of the ester linkages on said perfluorinated polyester to ether linkages; and
    c) hydrolyzing in the absence of sulfur tetrafluoride the ester linkages of said functional perfluoropolyether compound to produce a low molecular weight difunctional carboxylic acid.

* * * * *